(12) United States Patent
Taniguchi et al.

(10) Patent No.: US 10,866,296 B2
(45) Date of Patent: Dec. 15, 2020

(54) MAGNETIC RESONANCE IMAGING APPARATUS AND CALCULATION IMAGE GENERATION METHOD USING PULSE SEQUENCE

(71) Applicant: Hitachi, Ltd., Tokyo (JP)

(72) Inventors: Yo Taniguchi, Tokyo (JP); Hisaaki Ochi, Tokyo (JP); Toru Shirai, Tokyo (JP); Yoshihisa Sotome, Tokyo (JP); Suguru Yokosawa, Tokyo (JP); Tomoki Amemiya, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/342,111

(22) PCT Filed: Oct. 11, 2017

(86) PCT No.: PCT/JP2017/036823
§ 371 (c)(1),
(2) Date: Apr. 15, 2019

(87) PCT Pub. No.: WO2018/088096
PCT Pub. Date: May 17, 2018

(65) Prior Publication Data
US 2019/0250231 A1 Aug. 15, 2019

(30) Foreign Application Priority Data

Nov. 14, 2016 (JP) ................. 2016-221863

(51) Int. Cl.
*G01R 33/50* (2006.01)
*A61B 5/055* (2006.01)
*G01R 33/561* (2006.01)

(52) U.S. Cl.
CPC ............ *G01R 33/50* (2013.01); *A61B 5/055* (2013.01); *G01R 33/5618* (2013.01)

(58) Field of Classification Search
CPC ...... G01R 33/50; G01R 33/5618; A61B 5/055
See application file for complete search history.

(56) References Cited

U.S. PATENT DOCUMENTS 4,748,409 A * 5/1988 Frahm ................ G01R 33/4833
324/309
4,896,113 A * 1/1990 Pelc ....................... G01R 33/50
324/309

(Continued)

FOREIGN PATENT DOCUMENTS

EP          871038 A1    10/1998
JP        H01-221150 A    9/1989
(Continued)

OTHER PUBLICATIONS

English Translation of International Preliminary Report on Patentability issued in corresponding application No. PCT/JP2017/036823, dated May 14, 2019.

(Continued)

*Primary Examiner* — G. M. A Hyder
(74) *Attorney, Agent, or Firm* — Foley & Lardner LLP

(57) ABSTRACT

A plurality of subject parameter maps are acquired at high speed. In addition to using an imaging sequence for generating both a gradient echo and a spin echo in a single imaging sequence, one or more parameters such as the longitudinal relaxation time T1 and the apparent transverse relaxation time T2* are calculated using the gradient echo and another parameter such as true transverse relaxation time T2 is calculated using the spin echo. When a value of one parameter is calculated, a value of the parameter calculated at the time of calculating the other parameter can be used.

10 Claims, 9 Drawing Sheets

(56) References Cited

U.S. PATENT DOCUMENTS

| | | | | |
|---|---|---|---|---|
| 5,270,654 | A | * | 12/1993 | Feinberg ............ G01R 33/5615 |
| | | | | 324/307 |
| 5,594,336 | A | * | 1/1997 | Gullapalli .......... G01R 33/4828 |
| | | | | 324/309 |
| 5,603,319 | A | | 2/1997 | Kuhara et al. |
| 5,860,921 | A | * | 1/1999 | Ma ........................ G01R 33/50 |
| | | | | 600/410 |
| 5,869,964 | A | | 2/1999 | Kuhara et al. |
| 2008/0272779 | A1 | * | 11/2008 | Dahnke .............. G01R 33/5601 |
| | | | | 324/309 |

FOREIGN PATENT DOCUMENTS

| | | |
|---|---|---|
| JP | H04-170938 A | 6/1992 |
| JP | H06-054816 A | 3/1994 |
| JP | H07-079949 A | 3/1995 |
| JP | H09-066043 A | 3/1997 |
| JP | H11-000322 A | 1/1999 |
| JP | 2011-024926 A | 2/2011 |

OTHER PUBLICATIONS

International Search Report PCT/JP2017/036823, dated Jan. 16, 2018.

* cited by examiner

FIG.4
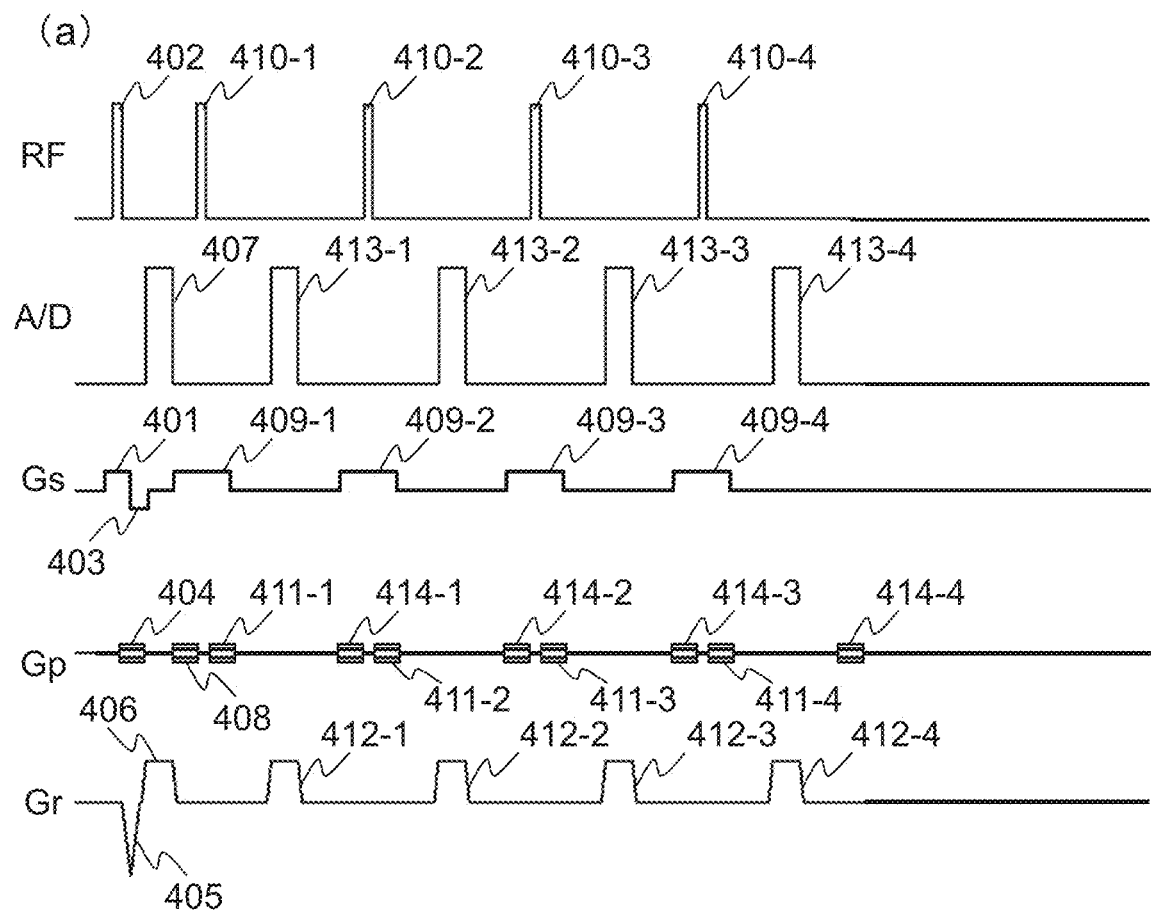
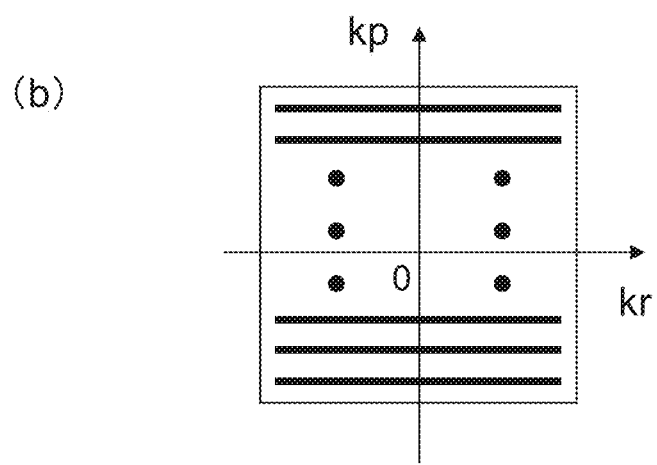

FIG.6

| IMAGING PARAMETER SET | FA (DEGREE) | θ (DEGREE) | TR (SECOND) | NUMBER OF INVERSION PULSE |
|---|---|---|---|---|
| P1 | 10 | 8 | 0.03 | 0 |
| P2 | 40 | 2 | 0.01 | 0 |
| P3 | 40 | 2 | 0.04 | 4 |
| P4 | 40 | 5 | 0.01 | 0 |
| P5 | 40 | 7 | 0.01 | 0 |
| P6 | 40 | 22 | 0.03 | 0 |

MAGNETIC RESONANCE IMAGING APPARATUS AND CALCULATION IMAGE GENERATION METHOD USING PULSE SEQUENCE

TECHNICAL FIELD

The present invention relates to a magnetic resonance imaging technique, and in particular to a technique for estimating a subject parameter by calculation.

BACKGROUND ART

A magnetic resonance imaging (MRI) apparatus acquires an image of atomic nuclear density (proton density) of a tissue and an images of a moving part such as blood flow, using signal intensity and phase information of a nuclear magnetic resonance signal obtained from an atom constituting the tissue of a subject, mainly an atomic nucleus of a hydrogen atom. The signal intensity and phase of the nuclear magnetic resonance signal are determined by the conditions at the time of imaging and characteristics of the apparatus and the tissue of the subject. Utilizing this fact, in recent years, in the magnetic resonance imaging apparatus, technologies for obtaining a specific characteristic, among the characteristics of the apparatus or the tissue of the subject, that the relationship with the nuclear magnetic resonance signal can be analyzed by calculation as a parameter and imaging the characteristic are widely used.

As one such technology, there is a method in which a plurality of images are captured with different imaging parameters and subject parameters and apparatus parameters are obtained by calculation for each pixel. Here, the imaging parameters are the repetition time, intensity of a high-frequency magnetic field, a phase of the high-frequency magnetic field, and the like, and the subject parameters are the longitudinal relaxation time, transverse relaxation time, spin density, resonance frequency, the diffusion coefficient, and irradiation intensity distribution of the high-frequency magnetic field, and the like. The apparatus parameters are magnetic field intensity, reception sensitivity distribution, and the like, but also depend on the subject. An image whose pixel value is a value of the obtained subject parameter is called a calculation image or a map.

In the magnetic resonance imaging, there are various imaging sequences according to the purpose of imaging parameter. Depending on the imaging sequence, the relationship (signal function) among the imaging parameter and the subject parameter or the apparatus parameter and the pixel value is analytically obtained, and, it is possible to calculate the subject parameter and the apparatus parameter by using this signal function. There has been proposed a method in which a calculation function can be generated by configuring a signal function by numerical simulation even in the imaging sequence in which the signal function is not analytically obtained (PTL 1).

PTL 1 discloses a procedure for acquiring respective maps such as the relaxation time, the frequency, the irradiation intensity of high-frequency magnetic field, the spin density, the resonance frequency, and the like as the subject parameter or apparatus parameter by using RF-spoiled GE which is a high-speed imaging sequence of a gradient echo (GE) system as an example.

CITATION LIST

Patent Literature

[PTL 1] JP-A-2011-024926

SUMMARY OF INVENTION

Technical Problem

There are two types of transverse relaxation time, which is one of the subject parameters, of longitudinal relaxation time T1 and transverse relaxation time T2. Furthermore, for the transverse relaxation time T2, there may be the case where T2 itself (true transverse relaxation time) is obtained or the case where the apparent transverse relaxation time T2* may be obtained depending on the imaging method. The T2* is the transverse relaxation time including the influence of non-uniformity of the static magnetic field, the T2* can be acquired in an imaging sequence of the GE type in which the non-uniformity of the static magnetic field is generated and the T2 can be acquired using a spin echo (SE) imaging sequence. In PTL 1, since the imaging sequence of the GE system is used, the calculated transverse relaxation time is T2*, and T2 cannot be acquired.

The T2 is a more important parameter than the T2* in grasping the state of the tissue, and a T2-weighted image is widely used in general clinical examinations than a T2*-weighted image. The T2-weighted image can be obtained by using the imaging sequence of SE type, but in general, the imaging sequence of the SE type has longer imaging time than the imaging sequence of the GE type. Further, if it is attempted to acquire not only the T2 but also the T2* and other parameters, a longer imaging time is required.

The present invention has been made in view of the circumstances described above, and an object thereof is to acquire a plurality of subject parameter maps at high speed.

Solution to Problem

In order to solve the problems described above, in the present invention, in addition to using an imaging sequence for generating both a gradient echo and a spin echo in a single imaging sequence, values of one or more parameters are calculated using the gradient echo, and values of other parameters are calculated using the spin echo. When calculating the value of one parameter, the value of the parameter obtained by calculation of the other parameter may be used.

That is, a magnetic resonance imaging apparatus of the present invention includes a measurement unit that applies a high-frequency magnetic field and a gradient magnetic field to a subject and measures a nuclear magnetic resonance signal emitted from the subject, a control unit that controls the measurement unit according to a pulse sequence, and a parameter calculation unit that calculates a parameter value of a subject parameter related to a characteristic of the subject using the nuclear magnetic resonance signal acquired by the measurement unit and the signal function of a pulse sequence, and in which the control unit controls the measurement unit by using the pulse sequence for measuring at least two types (kinds) of nuclear magnetic resonance signals after one application of a high-frequency magnetic field for excitation, as the pulse sequence, the parameter calculation unit calculates parameter values of one or more subject parameters including a first subject parameter using one of the two types of nuclear magnetic resonance signals and calculates parameter values of one or more subject parameters including a second subject parameter different from the first subject parameter using the other of the two types of nuclear magnetic resonance signals.

A calculation image generation method of the present invention is a method of generating a calculation image of a subject parameter relating to a characteristic of a subject by using echo signals acquired by executing a pulse sequence including a gradient echo measurement and a subsequent spin echo measurement a plurality of times while changing values of imaging parameters, the method including calculating two or more subject parameters including a first subject parameter by using the gradient echo obtained by imaging a plurality of times and a signal function of the pulse sequence and calculating a parameter value of a second parameter using the spin echo obtained by imaging a plurality of times and a signal function after the gradient echo measurement.

Advantageous Effects of Invention

According to the present invention, a plurality of parameters can be acquired at high speed by calculating parameters stepwise using a plurality of nuclear magnetic resonance signals obtained in a single imaging sequence. In the imaging sequence adopted by the present invention, it is possible to measure the spin echo for T2 calculation by using the waiting time after measuring the gradient echo. For that reason, it becomes possible to acquire the T2 map by restraining extension of the imaging time to the minimum.

BRIEF DESCRIPTION OF DRAWINGS

FIG. 4(a) is a view illustrating one embodiment of an imaging sequence, and FIG. 4(b) is a view illustrating k-space data consisting of echoes obtained in the imaging sequence.

FIG. 6 is a view illustrating an example of parameter sets.

DESCRIPTION OF EMBODIMENTS

Figure 1:
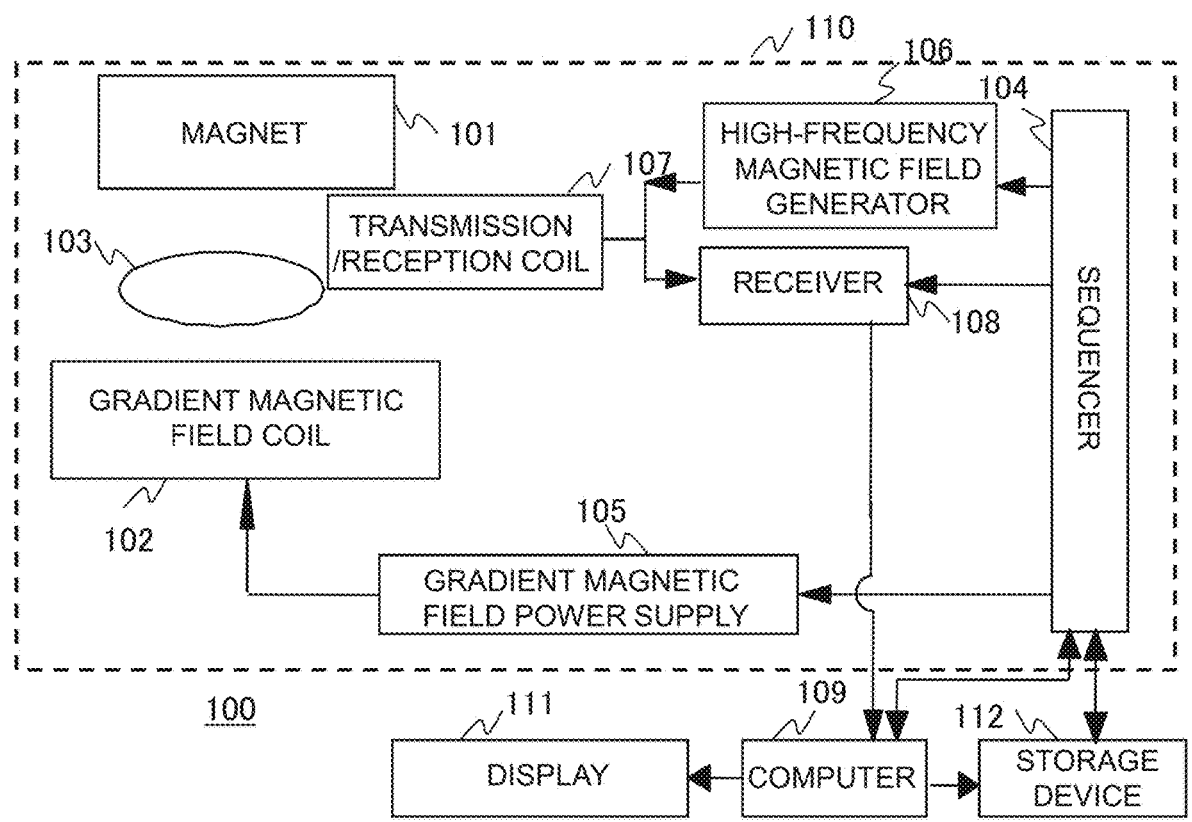
FIG. 1 is a diagram illustrating an overall configuration of a magnetic resonance imaging apparatus to which the present invention is applied.

Hereinafter, embodiments of the present invention will be described with reference to the drawings. In all the drawings for explaining the embodiments of the present invention, those having the same function are denoted by the same reference numerals, and repetitive description thereof is omitted.

<Apparatus Configuration>

An embodiment of a magnetic resonance imaging apparatus to which the present invention is applied will be described. FIG. 1 is a block diagram illustrating a schematic configuration of a magnetic resonance imaging apparatus 100 according to this embodiment. The magnetic resonance imaging apparatus 100 includes a magnet 101 for generating a static magnetic field, a gradient magnetic field coil 102 for generating a gradient magnetic field, a sequencer 104, a gradient magnetic field power supply 105, a high-frequency magnetic field generator 106, a transmission and reception coil 107 for irradiating a high-frequency magnetic field and detecting a nuclear magnetic resonance signal, a receiver 108, a computer 109, a display 111, and a storage device 112. Although the transmission and reception coil 107 is illustrated as a single coil in the drawing, the transmission coil and the reception coil may be separately provided. Hereinafter, the magnet 101, the gradient magnetic field coil 102, the gradient magnetic field power supply 105, the sequencer 104, the high-frequency magnetic field generator 106, the transmission and reception coil 107, and the receiver 108 are collectively referred to as a measurement unit 110.

A subject (for example, living body) 103 is placed on a bed (table) in a static magnetic field space generated by the magnet 101. In addition, the sequencer 104 sends an instruction to the gradient magnetic field power supply 105 and the high-frequency magnetic field generator 106 to generate the gradient magnetic field and the high-frequency magnetic field, respectively. The high-frequency magnetic field is applied to the subject 103 through the transmission and reception coil 107. The nuclear magnetic resonance signal generated from the subject 103 is received by the transmission and reception coil 107, and detection is performed by the receiver 108. A nuclear magnetic resonance frequency (detection reference frequency f0) used as a reference for detection is set by the sequencer 104. The detected signal is sent to the computer 109, where signal processing such as image reconstruction is performed. The result is displayed on the display 111. It is also possible to store the detected signal and the measurement condition in the storage device 112 as necessary.

The sequencer 104 normally performs control so that each apparatus operates with pre-programmed timing and intensity. Among the programs, those which describe the timing and intensity of the high-frequency magnetic field, the gradient magnetic field, signal reception are particularly called a pulse sequence (imaging sequence). In the magnetic resonance imaging apparatus of this embodiment, as will be described later, an imaging sequence for generating both a gradient echo and a spin echo is stored.

The computer 109 includes a CPU and a memory, and functions as a control unit that controls operations of the units described above, and also functions as an operation unit that performs various signal processing and arithmetic operation. Specifically, the measurement unit is operated according to the pulse sequence to measure the echo signal. The obtained echo signal is subjected to various signal processing to obtain a desired image. The image includes a calculation image having the subject parameter value as each pixel value. Programs and algorithms for control and an arithmetic operation are stored in the storage device 112. By loading and executing the program stored in the storage device 112 by the CPU of the computer 109, each function of the computer 109 is realized. A part of the functions of the computer 109 may be realized by hardware such as a programmable logic device (PLD) or the like.

Figure 2:
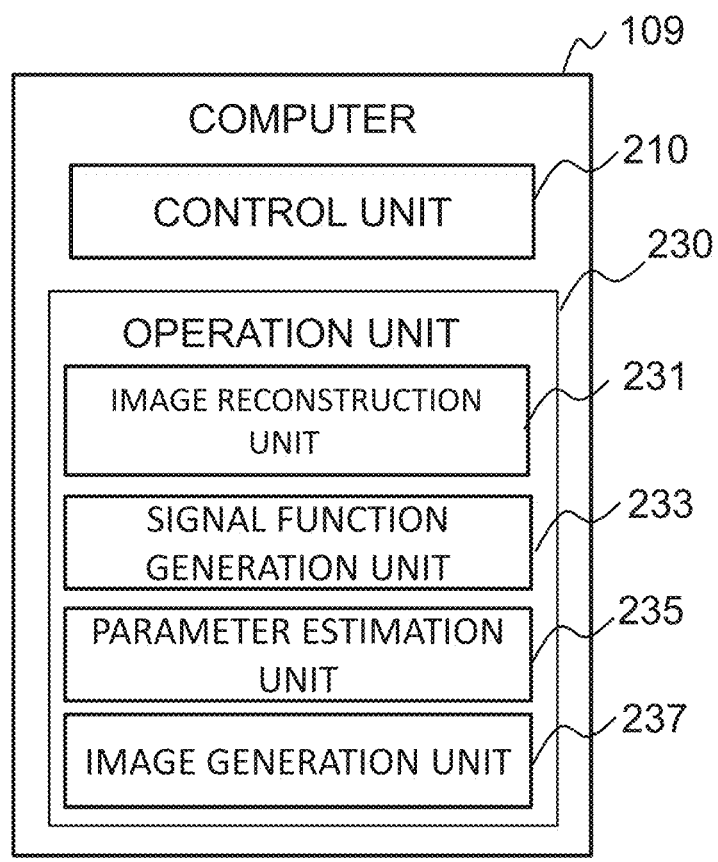
FIG. 2 is a functional block diagram of a computer.

A configuration example of the computer 109 for realizing the processing described above is illustrated in FIG. 2. As illustrated in the figure, the computer 109 includes a control unit 210 that controls the entire apparatus including the measurement unit and the operation unit, and an operation unit 230. The operation unit 230 includes an image reconstruction unit 231, a signal function generation unit 233, a parameter estimation unit 235, and an image generation unit 237. The signal function generation unit 233, the parameter estimation unit 235, and the image generation unit 237, which are functional units as the parameter calculation unit, of the respective functional units of the operation unit 230 may be realized by a computer provided separately from the magnetic resonance imaging apparatus 100 and capable of transmitting and receiving data to and from the computer 109 of the magnetic resonance imaging apparatus 100.

<Processing by Computer>

Figure 3:
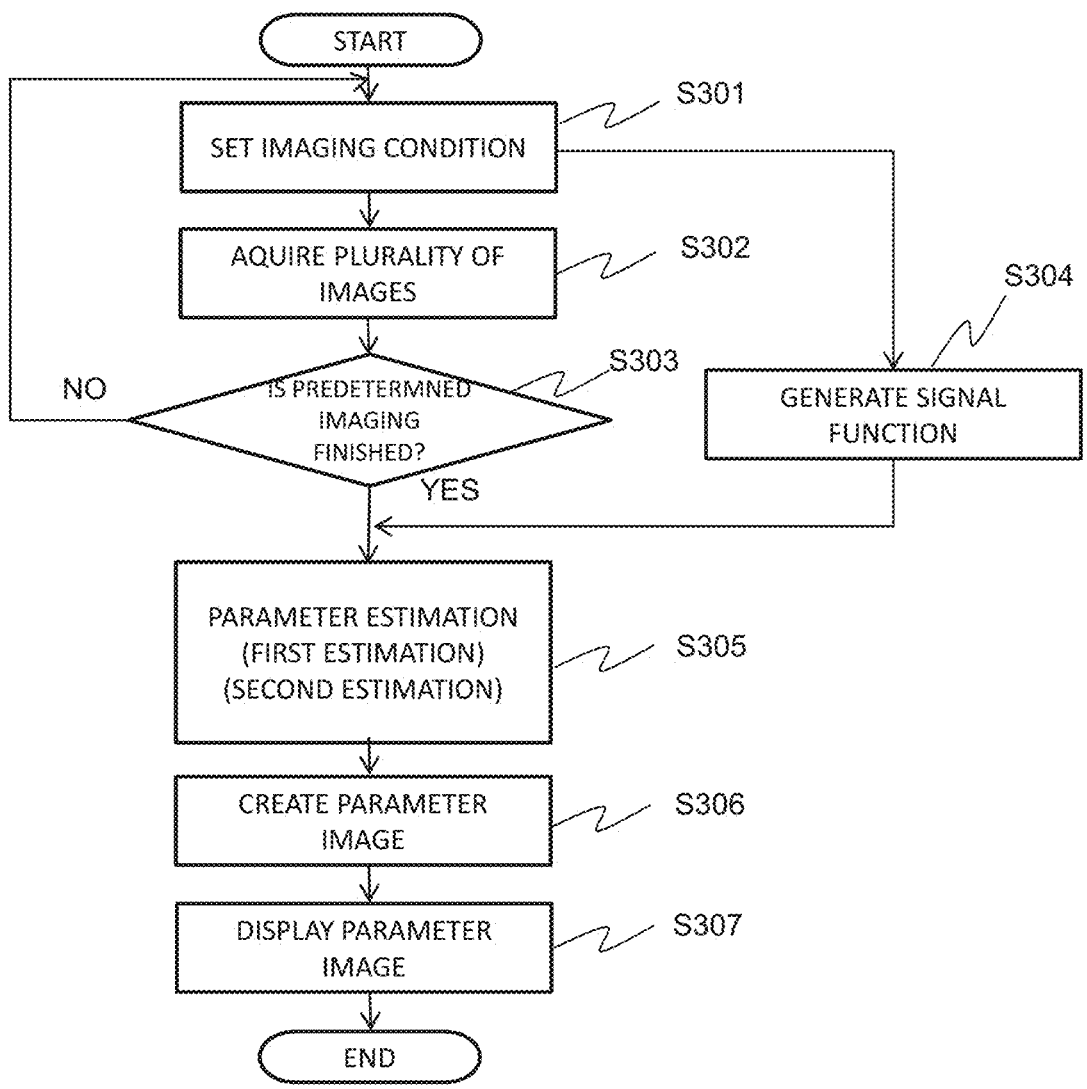
FIG. 3 is a flowchart illustrating an operation of the magnetic resonance imaging apparatus according to an embodiment.

Next, preparation of calculation image by the magnetic resonance imaging apparatus of this embodiment will be described. In this embodiment, as an example, a case of calculating a longitudinal relaxation time T1, transverse relaxation times T2 and T2*, irradiation magnetic field intensity ratio B1, and reception coil sensitivity Sc as parameters will be described. FIG. 3 illustrates an outline of a procedure for preparing a calculation image.

As a premise, combinations of a plurality of imaging conditions are determined in advance and stored in the storage device 112 (S301). The control unit 210 sets one of the plurality of imaging conditions, controls the measurement unit 110, execute a predetermined pulse sequence and performs imaging for measuring echo signals, here, a gradient echo and a spin echo (S302). For each echo signal, if the number of measurements required for image reconstruction is ended, imaging is performed while changing imaging conditions (S303). The imaging is repeated until all imaging of the combination of planned imaging conditions is completed. On the other hand, the computer 109 (signal function generation unit 233) generates the signal function when the imaging sequence used for imaging is decided (S304). The computer 109 (image reconstruction unit 231) reconstructs images (GE image and SE image) for each imaging with respect to two types of echo signals obtained by a plurality of imaging and the parameter estimation unit 235 estimates the parameters using the pixel values of these images and the signal function generated by the signal function generation unit 233 (S305). Apart of the arithmetic operations performed by the computer 109 may be performed in parallel with the imaging before the end of imaging. Also, if the imaging sequence is the same, the signal functions are the same even if the imaging conditions are different. For that reason, by storing the generated signal function, it is unnecessary to generate a signal function each time imaging is performed, and the same signal function can be repeatedly used.

The parameter estimation includes estimation (estimation of a first parameter) using the gradient echo and estimation (estimation of a second parameter) using the spin echo, and different types of parameters are calculated in each processing. The image generation unit 237 creates an image, that is, a calculation image (parameter image) whose pixel values are the parameter values for all or some of the plurality of computed parameters (S306). The image generation unit 237 creates a display image including a calculation image as a display image or further includes a calculation image and displays the display image on the display 111 (S307).

Details of each processing will be described below.

[Setting of Imaging Condition S301]

In this processing, an imaging sequence and an imaging condition are set. The imaging condition is a parameter (imaging parameter) arbitrarily settable by the user at the time of executing the imaging sequence, specifically, the repeat time (TR), the echo time (TE), setting intensity (Flip Angle (FA)) of the high-frequency magnetic field, an increment (θ) of the phase of the high-frequency magnetic field, and the like. In this embodiment, a plurality of combinations are created by making these values different.

First, the imaging sequence will be described. In this embodiment, as the imaging sequence, an imaging sequence for generating both the gradient echo and the spin echo after application of one excitation pulse is used. As such an imaging sequence, for example, a sequence (hereinafter, referred to as a GE-SE sequence) obtained by combining an RF spoiled GE sequence and an SE sequence can be used. The RF-spoiled GE sequence enables 3D imaging at high speed and the pixel values of the image obtained by this imaging sequence depends mainly on relaxation times T1 and T2* and spin density ρ, which are subject parameters, and B1 and Sc which are apparatus parameters.

An example of the GE-SE sequence is illustrated in FIG. 4(*a*). In FIG. 4(*a*), RF, A/D, Gs, Gp, and Gr respectively represent a high-frequency magnetic field, signal reception, a slice gradient magnetic field, a phase encoding gradient magnetic field, and a readout gradient magnetic field. In this figure, a case where the axis of the phase encoding gradient magnetic field Gp is uniaxial, but in the case of 3D-sequence, a biaxial phase encoding gradient magnetic field is used.

Figure 5:
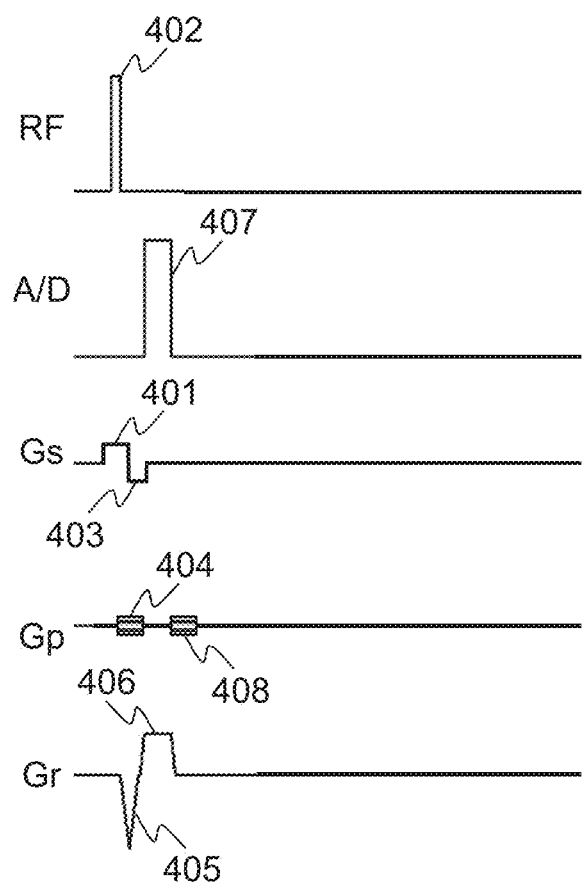
FIG. 5 is a view illustrating an RF-spoiled GE sequence.

This GE-SE sequence generates a spin echo by an inversion RF pulse by using the waiting time after echo measurement of the RF-spoiled GE sequence, and the sequence up to the gradient echo measurement is the same as the RF-spoiled GE sequence illustrated in FIG. 5. That is, first, along with application of the slice gradient magnetic field pulse 401, a high-frequency magnetic field (RF) pulse 402 is irradiated to excite magnetization of a certain slice in a target object. Next, after applying a slice rephase gradient magnetic field pulse 403, the phase encoding gradient magnetic field pulse 404, and a readout gradient magnetic field 405 for dephasing, a nuclear magnetic resonance signal (gradient echo, first echo) 407 is measured while applying the read out gradient magnetic field pulse 406. Finally, a phase encoding gradient magnetic field pulse 408 for dephasing is applied.

Next, along with the application of a slice gradient magnetic field pulse 409-1, an inversion pulse 410-1 is irradiated to invert magnetization in the slice. Then, after applying a phase encoding gradient magnetic field pulse 411-1, a nuclear magnetic resonance signal (spin echo, second echo) is measured 413-1 while applying a readout gradient magnetic field pulse 412-1. Finally, a phase encoding gradient magnetic field pulse 414-1 for dephasing is applied.

Thereafter, the same sequence as the sequence from the application of the slice gradient magnetic field pulse 409-1 to the application of the phase encoding gradient magnetic field pulse 414-1 for dephasing is repeated as many times as necessary. In the example of FIG. 4(*a*), a total of four spin echoes are measured (413-1 to 413-4) from the second echo to the fifth echo by applying a total of four inversion pulses (410-1 to 410-4). The procedure from irradiation of the RF pulse 402 to last spin echo measurement is repeated at the repetition time TR, and each echo from the first echo to the fifth echo is measured a plurality of times. The intensities (phase encoding amount kp) of the phase encoding gradient magnetic field pulses (404, 408, 411-1 to 411-4, and 414-1 to 414-4) are changed for each repetition and an incremental value of the phase of the RF pulse 402 is changed by θ (the phase θn of the n-th RF pulse is $\theta_n = \theta_{n-1} + \theta \times n$). By incrementing the phase of RF by a predetermined amount at each repetition, the effect of transverse relaxation can be reduced.

The number of inversion pulses of the GE-SE sequence is arbitrary. However, when the repetition time is as short as several tens of milliseconds, it is desirable that it is an even number. This is to shorten the imaging time by shortening the waiting time required until the next excitation, similar to the RF-spoiled GE. That is, in the RF-spoiled GE, magnetization excited by the excitation pulse is designed so that a longitudinal magnetization component oriented in the direction of the static magnetic field remains to some extent and the waiting time to the next excitation pulse can be shortened. Here, when the inversion pulse is irradiated, the longitudinal magnetization is inverted, and when it is irradiated once again, it returns to the direction of the original static magnetic field. As such, by setting the inversion pulse to an even number, the longitudinal magnetization can be oriented in the direction of the static magnetic field before the next excitation pulse, similar to the RF-spoiled GE, also in this sequence.

In this embodiment, in order to obtain a predetermined number of gradient echo images, the RF-spoiled GE not using an inversion pulse is also used.

Next, a combination (imaging parameter set) of imaging parameters will be described. The imaging parameter set is one obtained by respectively combining imaging parameters such as the flip angle (FA), repetition time (TR), echo time (TE), inversion pulse interval, θ (RF phase increment value) as predetermined parameter values, and a plurality of different imaging parameter sets are determined in advance and imaging is performed with different imaging parameter sets. As for the combination, it is not necessary to make the values of all the parameters described above different, values of some of the parameters may be fixed, and only some of the parameter values may be different. The combination can be selected as a combination of the values of each parameter, based on, for example, the law of error propagation, so as to minimize the influence of noise.

The value of the parameter is determined in consideration of the type of the subject parameter to be calculated and the like. For example, the FA is set to approximately 5 to 60 degrees in a usual RF-spoiled GE, but in this embodiment, it is made as small as possible. This is due to the following reason. When the FA is large, the magnetization transfer effect becomes large and thus, signal intensity tends to be small due to the influence of the protein. As a result, the estimated values of T1 and T2 are also influenced by protein concentration, and T1 and T2 which are different from the case of individually measuring T1 and T2 can be obtained by a normal method. In order to suppress the influence of the magnetization transfer effect, it is desirable to suppress the maximum value of FA to approximately 40 degrees. However, this is not applied in a case when it is desired to measure T1 and T2 taking into consideration the influence of the magnetization transfer effect.

The maximum value of TR is determined in consideration of the imaging sequence to be used, the number of inversion pulses, and the like. For example, since an inversion pulse is added to the RF-spoiled GE in the GE-SE sequence, the TR becomes longer than the RF-spoiled GE. For that reason, it is better to set the imaging parameter set that uses the GE-SE sequence to have a long TR. Increasing the inversion pulse interval and TR of the GE-SE sequence improves estimation accuracy of long T2, but takes longer imaging time.

The phase increment θ of the RF pulse changes the phase of the RF pulse in order to make the influence of the transverse relaxation different, and it is possible to obtain a signal with different influence of transverse relaxation by changing the phase increment θ. In general, the influence of transverse relaxation disappears by setting the phase increment to about 20 degrees and thus, the increment is changed within the range equal to or less than that. The TE and inversion pulse interval are determined in consideration of constraints in the apparatus and the SAR. These imaging parameters may be fixed values.

The number of imaging parameter sets is equal to or greater than the number of parameters (the number of unknowns) to be estimated in parameter estimation to be described later. In this embodiment, since the number of unknowns is 4 (T1, T2, B1, and Sc), the number of the imaging parameter sets is set to 4 or more. As the number of parameter sets, that is, the number of images obtained by imaging the parameter set increases, estimation accuracy improves, but the imaging time becomes longer correspondingly.

An example of a parameter set selected to minimize noise based on the law of error propagation is illustrated in FIG. 6. In this example, six imaging parameter sets P1 to P6 composed of combinations when the FA is set to 10 degrees and 40 degrees, θ is set to 2 degrees, 5 degrees, 7 degrees, 8 degrees, and 22 degrees, and the TR is set to 10 ms, 30 ms, and 40 ms are determined. In this imaging parameter sets P1 to P6, all of the TEs of the gradient echoes are set to 3 ms. As for the imaging sequence, the GE-SE sequence of FIG. 4($a$) is set for P3 having the longest TR and the RF-spoiled GE of FIG. 5 is set for other imaging parameter sets. Also, the interval between the inversion pulses of the GE-SE sequence is 8 ms.

[Imaging S302 and S303]

Figure 7:
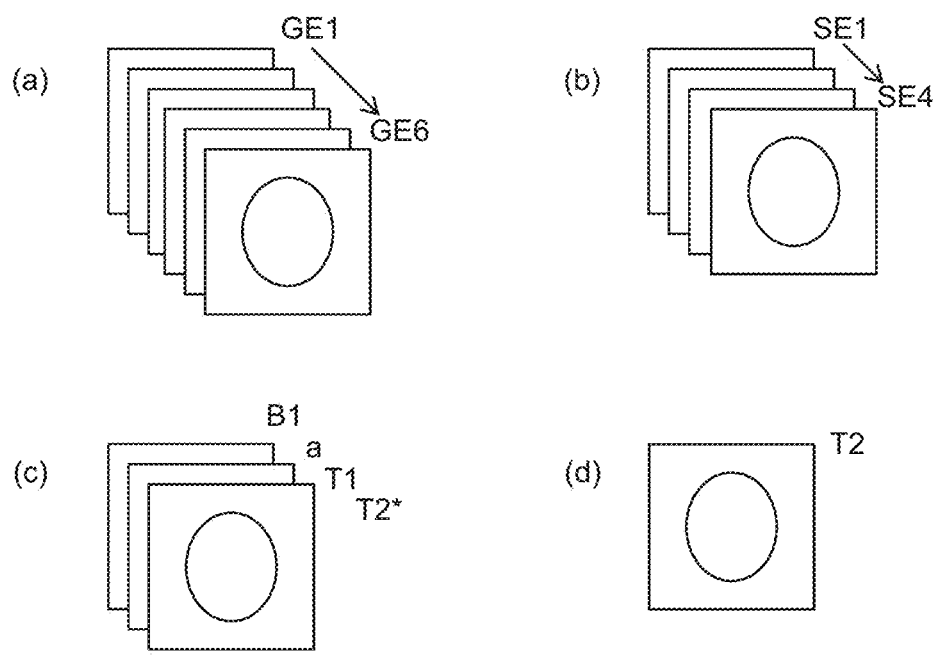
FIG. 7(a) and FIG. 7(b) are views respectively illustrating images obtained in the parameter sets of FIG. 6, and FIG. 7(c) and FIG. 7(d) are views respectively illustrating a calculation image obtained from the image of (a) and a calculation image obtained from the image of (b).

Under the control of the control unit 210, the measurement unit 110 captures a plurality of images using the plurality of imaging parameter sets described above. That is, imaging is performed a plurality of times while changing the imaging parameter set to obtain a plurality of gradient images (GE images) and a plurality of spin echo images (SE images). For example, the echoes obtained by the GE-SE sequence in FIG. 4($a$) are arranged in the k space as illustrated in FIG. 4($b$) for each echo number, and the image is reconstructed by being subjected to two-dimensional inverse Fourier transform. For example, a first echo image is reconstructed from a first echo and a second echo image is reconstructed from a second echo. The first echo image is a GE image and the second and subsequent echo images are SE images. In the case of RF-spoiled GE by which one gradient echo is obtained with one repetition illustrated in FIG. 5, one GE image can be obtained by one imaging. In a plurality of imaging using the parameter sets illustrated in FIG. 6, six GE images and four SE images are obtained as illustrated in FIGS. 7($a$) and 7($b$).

Figure 8:
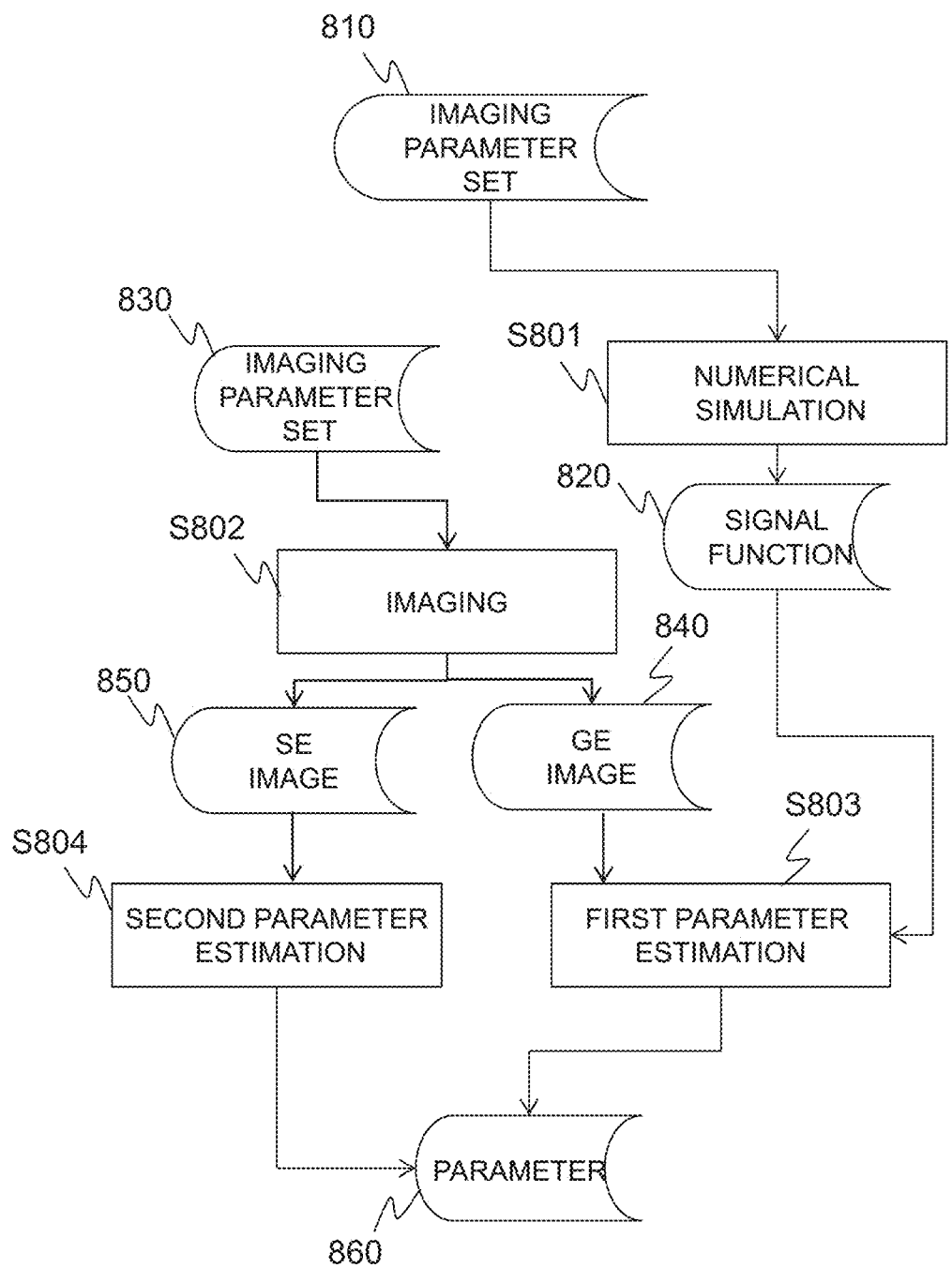
FIG. 8 is a diagram illustrating the relationship between each process of an operation unit and input and output data.

[Parameter Calculation S304 and S305] The operation unit 230 calculates the subject parameter and the apparatus parameter using the plurality of images acquired as described above. Hereinafter, the processing of the operation unit 230 related to parameter calculation will be described with reference to FIG. 8. FIG. 8 is a diagram illustrating the relationship between each processing and input and output data.

[Signal Function Generation (Numerical Simulation) S801]

When the imaging sequence is determined, the signal function generation unit 233 generates a function (signal function) representing signal intensity of each pixel obtained by the imaging sequence by numerical simulation. In this embodiment, the signal function of the GE-SE sequence is generated. The signal function fs is a function of imaging parameters (FA, TR, TE, and θ), apparatus parameters, and subject parameters, and is expressed as follows.

$$I = f_s(\rho, T1, T2, B1, FA, TR, TE, \theta, Sc) \quad (1)$$
$$= \rho Sc\exp(-TE/T2)f(T1, T2, B1 \times FA, \theta, TR)$$

Here, T1, T2, and ρ are the longitudinal relaxation time, transverse relaxation time, and spin density of the subject parameter, respectively, and B1 and Sc are irradiation intensity of the RF and sensitivity of the receiving coil which are parameters (here, referred to as the apparatus parameter) depending on the characteristic of the apparatus and the characteristic of the subject. Here, since B1 is a coefficient of the FA at the time of imaging, the B1 is converted into a product form with FA. Since the ρ and Sc act on the signal intensity as a proportionality coefficient, the ρ and Sc are placed outside the function, and since the TE also exerts the signal intensity in exponential form of exponential function, it is similarly placed outside the function. As a result, an expression (1) can be rewritten as in a second-stage equation.

In order to create a signal function fs 820, a function f which is the basis of fs is created by numerical simulation. That is, an arbitrary value is set to the subject parameters T1 and T2 after the spin density ρ of an object to be measured and B1 and Sc are set to 1 and the TE is set to 0, and the signal is calculated by numerical simulation by exhaustively changing the imaging parameters FA, TR, and θ for the set values. A range of parameter values to be changed is set to include a range of imaging parameters used for actual imaging (FIG. 3: S302) and the range of T1 and T2 of the subject. Examples of respective parameter values of the imaging parameter and the subject parameter are illustrated below. The number after the parameter is the number to be changed, the numerical value after the ":" is the parameter value.

TR 4 pieces [ms]: 10, 20, 30, 40
FA 10 pieces [degree]: 5, 10, 15, 20, 25, 30, 35, 40, 50, 60
θ 17 pieces [degree]: 0, 1, 2, 3, 4, 5, 6, 7, 8, 9, 10, 12, 14, 16, 18, 20, 22
T2 17 pieces [s]: 0.01, 0.02, 0.03, 0.04, 0.05, 0.07, 0.1, 0.14, 0.19, 0.27, 0.38, 0.53, 0.74, 1.0, 1.4, 2.0, 2.8
T1 15 pieces [s]: 0.05, 0.07, 0.1, 0.14, 0.19, 0.27, 0.38, 0.53, 0.74, 1.0, 1.5, 2.0, 2.8, 4.0, 5.6

The imaging parameter sets 810 (in the example described above, 173400 sets) composed of all combinations of these imaging parameters and subject parameters are constructed, and the respective signal values are calculated by computer simulation.

In the numerical simulation, a subject model in which spins are arranged on lattice points, and an imaging sequence, imaging parameters, and apparatus parameters are input, and Bloch's equation which is a fundamental equation of the magnetic resonance phenomenon is solved to output a magnetic resonance signal. The subject model is given as spatial distribution of spins (γ, $M_0$, T1, and T2). Here, γ is a gyromagnetic ratio, $M_0$ is thermal equilibrium magnetization (spin density), and T1 and T2 are the longitudinal relaxation time and the transverse relaxation time, respectively. By performing image reconstruction of the magnetic resonance signals, images under given conditions can be obtained.

The Bloch's equation is a first order linear ordinary differential equation, and it is expressed by the following equation.

$$\frac{d}{dt}\begin{pmatrix} M_x \\ M_y \\ M_z \end{pmatrix} = \begin{pmatrix} -1/T2 & \gamma H & \\ -\gamma H & -1/T2 & \gamma H_1 \\ & -\gamma H_1 & -1/T1 \end{pmatrix}\begin{pmatrix} M_x \\ M_y \\ M_z \end{pmatrix} + \begin{pmatrix} 0 \\ 0 \\ M_0/T1 \end{pmatrix} \quad (2)$$

$$H = B_0 + G_x x + G_y y + G_z z + 2\pi\Delta f_0/\gamma$$

Here, (x, y, z) represents a three-dimensional orthogonal coordinate system, and z is equal to the direction of the static magnetic field (intensity is $B_0$). Also, ($M_x$, $M_y$, $M_z$) is the spins, $G_x$, $G_y$, and $G_x$ are the gradient magnetic field intensities in the subscript direction, respectively, H1 is the high-frequency magnetic field intensity, and $\Delta f_0$ is the frequency of a rotating coordinate system.

The signal function f is created by interpolation from the signal values obtained by the computer simulation described above, and the fs 820 is created according to the expression (1). It is possible to use linear interpolation or spline interpolation of approximately 1st-order to 3rd-order for interpolation.

The signal function fs can also be expressed by the following expression (3) obtained by modifying the expression (1).

$$I = a\ \exp(-TE/T2)f(T1,T2,\theta,B1 \times FA,TR)$$
$$a = \rho S_c \quad (3)$$

Figure 9:
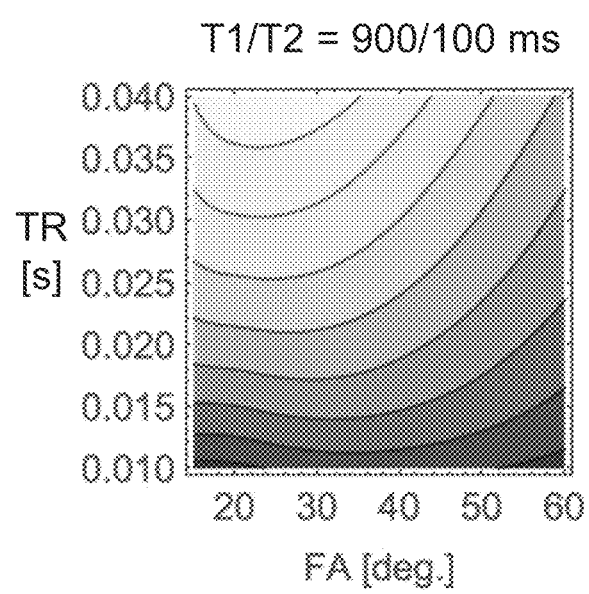
FIG. 9 is a diagram illustrating a part of a signal function.

Apart of the signal function f created as described above is illustrated in FIG. 9. The signal function f obtained by the simulation described above is a five-dimensional function with TR, FA, θ, T1, and T2 as variables. In FIG. 9, the signal intensities of a two-dimensional function in which T1, T2, and θ are constant (T1=900 ms, T2=100 ms, θ=5 degrees), and the horizontal axis and the vertical axis represent FA and TR, respectively, are illustrated.

[Estimation of Parameters]

In the parameter estimation, the subject parameters T1 and T2 (T2*) of the subject actually measured and a product a (=ρ×Sc) of ρ and apparatus parameter (reception sensitivity distribution) Sc are calculated using the images 840 and 850 for each echo obtained by imaging (S802) using the plurality of imaging parameter sets 530 and the signal function 820 of the imaging sequence. The T2* is estimated using the GE image, the T2 is estimated using the SE image (first parameter estimation), and the T2 is estimated using the SE image (second parameter estimation).

[First Parameter Estimation S803]

The T1 and T2, B1, and a are estimated using a plurality of GE images and the signal function 820 generated in the signal function generation S801. Specifically, the signal value I for each pixel is fitted to the signal function fs (expression (3)) generated in S801 to estimate T1 and T2, B1, and a which are unknowns. The function fitting can be performed by the least square method expressed by an expression (4).

$$\chi^2 = \sum_{FA,\Delta\theta,TR} \{I(FA, \theta, TR, TE) - \quad (4)$$
$$a\exp(-TE/T2)f(T1, T2, \theta, B1 \times Fa, TR)\} = \min$$

In the expression (4), I is a pixel value of an image obtained with a predetermined imaging parameter set (FA, θ, TR, and TE), and χ is the sum of the residuals of the pixel values of the image and the values calculated by substituting the estimated T1 and T2, B1, and a into the signal function of the expression (3). The T1 and T2, B1, and a which minimize the sum of the residuals are estimated. The estimated T2 is T2* since a gradient echo image is used as the original image. Then, the estimated T1 and T2*, B1, and a are output as a parameter 860. Since the parameter is calculated as a numerical value for each pixel, it is a map of each parameter, that is, a calculation image. In this example, as illustrated in FIG. 7(*c*), the calculation images of four parameters are obtained. Since the reception sensitivity distribution Sc (=a/ρ) can be easily measured by using an existing method in a general MRI apparatus, the spin density ρ can be obtained from the Sc and a.

[Second Parameter Estimation S804]

Next, the T2 is estimated using a plurality of spin echo images 850. In the parameter estimation using the SE image, an expression (5) representing T2 attenuation of the MR signal is used as a signal function.

$$I=a' \exp(-TE/T2) \quad (5)$$

$$a'=af(T1,T2,B1 \times FA, \theta, TR) \quad (6)$$

In the example of the imaging sequence illustrated in FIG. 4(*a*), four images SE1 to SE4 using the second echo to the fifth echo are obtained as illustrated in FIG. 7(*b*), and the T2 and a' are estimated by fitting the signal value I for each pixel of these images to the expression (5). The TEs of the four images SE1 to SE4 are, for example, 8 ms, 16 ms, 24 ms, and 32 ms, respectively, when the inversion pulse interval is 8 ms. Further, as the T1, the T1 calculated in the first parameter estimation S803 can be used. Similar to the first estimation, the function fitting can be performed by the least square method of minimizing the residual between the pixel value of the image obtained by measurement and the value calculated from the signal function (5).

Unlike the T2* obtained by the first parameter estimation, the T2 thus estimated is a "true transverse relaxation time" which is not influenced by non-uniformity of the static magnetic field. The parameter estimation unit 235 outputs the T2 as a parameter. The "a'" among the parameters estimated in the second parameter estimation S804 is expressed using the parameters a and T1, T2 (T2*), and B1 estimated in the first parameter estimation S803 as illustrated in an expression (6). Accordingly, in the second parameter estimation S804, as a correct value of "a'", only T2 may be estimated after giving the values of the a and T1, T2 (T2*), and B1 calculated in S803 in advance. With this configuration, the number of unknowns decreases from two to one and thus, estimation accuracy of the T2 improves. The matters described as above are the parameter estimation processing S305 in FIG. 3.

[Image Generation S306 and S307]

The image generation unit 237 generates a calculation image having the parameter values of the estimated parameters (T1, T2, T2*, a (=Sc×ρ), and B1) as pixels. The calculation image may be generated for all the estimated parameters or for some of the parameters. Alternatively, the T1 image or the T2/T2* image may be used to generate a T1-weighted image or a T2/T2*-weighted image.

The image generation unit 237 displays the generated calculation image or weighted image on the display 111 in various display forms. The display form may be, for example, a calculation image in which the pixel values are represented by black and white shades or may be displayed in color. Alternatively, the calculation image alone may be displayed, or it may be displayed in parallel with the proton density image obtained in imaging (S302). It is also possible to display a parameter value or a range of values of a specific part as a numerical value.

As described above, according to this embodiment, it is possible to acquire two types of echoes of the GE echo and SE echo without extending the whole imaging time, by performing an imaging sequence for acquiring the spin echo using the waiting time of the GE sequence. With this configuration, it is possible to acquire a T2 map in addition to various maps of the T1, T2*, a (=Sc×ρ), and B1.

Modification Example 1

In the embodiment described above, the number of spin echoes acquired in the GE-SE sequence is 4, but this number is arbitrary as long as it is 1 or more. For example, in the second parameter processing S804, when the result calculated in the first parameter estimation processing S803 is given as the correct value of "a'" in advance to estimate the T2, since only one unknown is the T2, the number of spin echoes may be 1 or more. Also, when two of the "a'" and T2 are estimated, it is necessary that the number of spin echoes is 2 or more. Also, in order to increase the estimation accuracy, the larger the number of spin echoes, the better. Practically, it is desirable that the number is 3 or more.

Modification Example 2

In the embodiment described above, the example in which the pulse interval of the inversion pulse in the GE-SE sequence is fixed has been described, but the imaging with different parameter sets may be added for the inversion pulse interval. In that case, if the number of spin echoes in the GE-SE sequence is 4, eight images with different TEs of the spin echo SE can be obtained and thus, the estimation accuracy of the subject parameter can be improved. Alternatively, it is possible to reduce the number of spin echoes in the GE-SE sequence and shorten the imaging time. Also, the number of spin echoes need not necessarily be equal in the parameter set of different inversion pulse intervals.

Modification Example 3

In the embodiment described above, the imaging sequence for measuring one gradient echo is adopted in the short parameter set (for example, P1, P2, P4 to P6 in FIG. 6) of the TR, but in the RF-spoiled GE of FIG. 5, it is also possible to use a multi-echo sequence for measuring gradient echoes of the second echo, third echo, and the like following the first echo 407. In this case, by applying the same phase encoding as the first echo to the second echo and subsequent echoes, it is possible to acquire the images of echoes different in TE. With this configuration, accuracy of estimation of the subject parameter can be improved similarly to the modification example 2.

Modification Example 4

In this embodiment, the B1, T1, T2* and a are calculated in the first parameter estimation S803 and the a (a') and T2 are calculated in the second parameter estimation S804, but the parameters other than the T2* and T2 may be estimated by any processing. However, by using the parameter estimated in one processing for the other estimation processing, it is possible to reduce the number of unknowns, reduce the number of necessary images (for example, the number of spin echoes), and shorten the imaging time.

As described above, although the modification examples of the present invention have been described, these modification examples can also be appropriately combined and applied as long as the modification examples do not conflict technically. Further, the present invention is not limited to the embodiment and its modification examples described above, and matters that some of the elements illustrated in the embodiments are omitted or additional elements are added are also included in the present invention.

REFERENCE SIGNS LIST

100: magnetic resonance imaging apparatus
101: magnet for generating a static magnetic field
102: gradient magnetic field coil
104: sequencer
105: gradient magnetic field power supply
106: high-frequency magnetic field generator
107: transmission and reception coil
108: receiver
109: computer
111: display
112: storage device
210: control unit
230: operation unit

The invention claimed is:

1. A magnetic resonance imaging apparatus comprising:
a measurement unit configured to apply a high-frequency magnetic field and a gradient magnetic field to a subject and measures a nuclear magnetic resonance signal emitted from the subject;
a control unit configured to control the measurement unit according to a pulse sequence; and
a parameter calculation unit configured to calculate a parameter value of a subject parameter related to a characteristic of the subject using the nuclear magnetic resonance signal acquired by the measurement unit and a signal function of the pulse sequence,
wherein the control unit is configured to control the measurement unit by using a pulse sequence for measuring at least two types of nuclear magnetic resonance signals including a gradient echo and a spin echo after one application of a high-frequency magnetic field for excitation, as the pulse sequence,
the parameter calculation unit is configured to calculate parameter values of one or more subject parameters including an apparent transverse relaxation time T2* using the gradient echo and to calculate parameter values of one or more subject parameters including a transverse relaxation time (true transverse relaxation time) T2 using the spin echo, and when calculating the apparent transverse relaxation time T2*, the parameter calculation unit uses a signal function generated in advance by a numerical simulation in which a number of imaging conditions are set for the pulse sequence.

2. The magnetic resonance imaging apparatus according to claim 1, further comprising:
a signal function generation unit configured to generate the signal function of the pulse sequence.

3. The magnetic resonance imaging apparatus according to claim 1,
wherein the parameter calculation unit is configured to calculate a transverse relaxation time T2 that is a true transverse relaxation time using a subject parameter other than the apparent transverse relaxation time T2* calculated when calculating the apparent transverse relaxation time T2* and the spin echo.

4. The magnetic resonance imaging apparatus according to claim 1,
wherein the pulse sequence is an imaging sequence in which an inverted RF pulse is added to an RF spoiled-GE sequence.

5. The magnetic resonance imaging apparatus according to claim 1,
wherein the control unit is configured to control the measurement unit to perform a plurality of measurements by using a plurality of parameter sets having different combinations of parameter values of a plurality of predetermined imaging parameters.

6. The magnetic resonance imaging apparatus according to claim 5, further comprising:
a storing unit configured to store the plurality of parameter sets determined in advance.

7. The magnetic resonance imaging apparatus according to claim 5,
wherein the plurality of imaging parameters include any one of a flip angle (FA) of the high-frequency magnetic field for excitation, a phase increment (θ) of the high-frequency magnetic field for excitation, or a repetition time (TR) of the pulse sequence.

8. A calculation image generation method of generating a calculation image of a subject parameter relating to a characteristic of a subject,
using a pulse sequence for measuring at least two types of nuclear magnetic resonance signals including a gradient echo and a spin echo after one application of a high-frequency magnetic field for excitation, as the pulse sequence;
calculating parameter values of one or more subject parameters including an apparent transverse relaxation time T2* using the gradient; and
calculating parameter values of one or more subject parameters including a transverse relaxation time T2 that is a true transverse relaxation time using the spin echo, and when calculating the apparent transverse relaxation time T2*, using a signal function generated in advance by numerical simulation in which a number of imaging conditions are set for the pulse sequence.

9. The calculation image generation method according to claim 8, further comprising:
generating a signal function of the pulse sequence.

10. The calculation image generation method according to claim 8,
wherein calculating a transverse relaxation time T2 that is the true transverse relaxation time comprises using a subject parameter other than the apparent transverse relaxation time T2* calculated when calculating the apparent transverse relaxation time T2* and the spin echo.

* * * * *